(12) United States Patent
Sander

(10) Patent No.: US 10,799,364 B2
(45) Date of Patent: Oct. 13, 2020

(54) REVISION IMPLANT AUGMENTS, SYSTEMS, AND METHODS

(71) Applicant: Wright Medical Technology, Inc., Memphis, TN (US)

(72) Inventor: Elizabeth J. Sander, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 178 days.

(21) Appl. No.: 16/169,187

(22) Filed: Oct. 24, 2018

(65) Prior Publication Data

US 2019/0083268 A1 Mar. 21, 2019

Related U.S. Application Data

(60) Continuation of application No. 15/455,696, filed on Mar. 10, 2017, now Pat. No. 10,226,351, which is a
(Continued)

(51) Int. Cl.
*A61F 2/42* (2006.01)
*A61F 2/30* (2006.01)
(Continued)

(52) U.S. Cl.
CPC ............ *A61F 2/30734* (2013.01); *A61F 2/42* (2013.01); *A61F 2/4202* (2013.01); *A61F 2/46* (2013.01);
(Continued)

(58) Field of Classification Search
CPC ....................... A61F 2/4202; A61F 2002/4207
See application file for complete search history.

(56) References Cited

U.S. PATENT DOCUMENTS

| | | | |
|---|---|---|---|
| 4,309,778 A | 1/1982 | Buechel et al. | |
| 2002/0055744 A1* | 5/2002 | Reiley | A61B 17/15 606/79 |

(Continued)

FOREIGN PATENT DOCUMENTS

| | | |
|---|---|---|
| CN | 103393461 A | 11/2013 |
| EP | 1433444 A1 | 6/2004 |

(Continued)

OTHER PUBLICATIONS

Office Action issued in connection with corresponding Japanese patent application No. 2016-535700, dated Nov. 21, 2017, 4 pages.
(Continued)

*Primary Examiner* — Suba Ganesan
(74) *Attorney, Agent, or Firm* — Duane Morris LLP

(57) ABSTRACT

A revision implant component comprising a body having a plurality of screw holes and a tapered head configured to engage a talar dome component of a multi-component ankle prosthesis. A surgical method is disclosed which includes creating an incision in a patient, exposing a multi-component ankle prosthesis implanted in a patient, disassembling at least one component of the multi-component ankle prosthesis, affixing a revision implant component to non-damaged bone using screws, and coupling the revision implant component to a talar dome of the multi-component ankle prosthesis.

13 Claims, 5 Drawing Sheets

Related U.S. Application Data division of application No. 14/403,829, filed as application No. PCT/US2014/052301 on Aug. 22, 2014, now Pat. No. 9,622,871.

(51) Int. Cl.
*A61F 2/46* (2006.01)
*A61B 17/80* (2006.01)
*A61B 17/86* (2006.01)

(52) U.S. Cl.
CPC .......... *A61B 17/8052* (2013.01); *A61B 17/86* (2013.01); *A61F 2/30771* (2013.01); *A61F 2002/3069* (2013.01); *A61F 2002/30332* (2013.01); *A61F 2002/30616* (2013.01); *A61F 2002/30736* (2013.01); *A61F 2002/30774* (2013.01); *A61F 2002/30784* (2013.01); *A61F 2002/4207* (2013.01); *A61F 2002/4619* (2013.01); *A61F 2002/4677* (2013.01); *A61F 2220/0008* (2013.01)

(56) References Cited

U.S. PATENT DOCUMENTS

| | | |
|---|---|---|
| 2003/0216813 A1 | 11/2003 | Ball et al. |
| 2004/0122523 A1 | 6/2004 | Guzman |
| 2004/0143336 A1 | 7/2004 | Burkinshaw |
| 2005/0107882 A1 | 5/2005 | Stone et al. |
| 2005/0288792 A1 | 12/2005 | Landes |
| 2006/0100714 A1 | 5/2006 | Ensign |
| 2008/0140130 A1 | 6/2008 | Chan et al. |
| 2009/0182433 A1 | 7/2009 | Reiley et al. |
| 2009/0192621 A1 | 7/2009 | Winslow et al. |
| 2011/0166608 A1 | 7/2011 | Duggal et al. |
| 2012/0271430 A1 | 10/2012 | Arnett et al. |
| 2014/0350688 A1 | 11/2014 | Michel et al. |

FOREIGN PATENT DOCUMENTS

| | | |
|---|---|---|
| EP | 1591084 A1 | 11/2005 |
| JP | S56-83343 A | 7/1981 |
| JP | 2004-000534 A | 1/2004 |
| JP | 2005-500123 A | 1/2005 |
| JP | 2013-526375 A | 6/2013 |
| WO | 2011146617 A2 | 11/2011 |
| WO | 2013086172 A1 | 6/2013 |
| WO | 2014160703 A2 | 10/2014 |

OTHER PUBLICATIONS

International Search Report and Written Opinion of the International Searching Authority, issued for PCT patent application No. PCT/US2014/052301, dated May 13, 2015, 12 pages.

Patent Examination Report No. 1 dated Mar. 24, 2016, for corresponding Australian patent application No. 2014318028, 8 pages.

\* cited by examiner

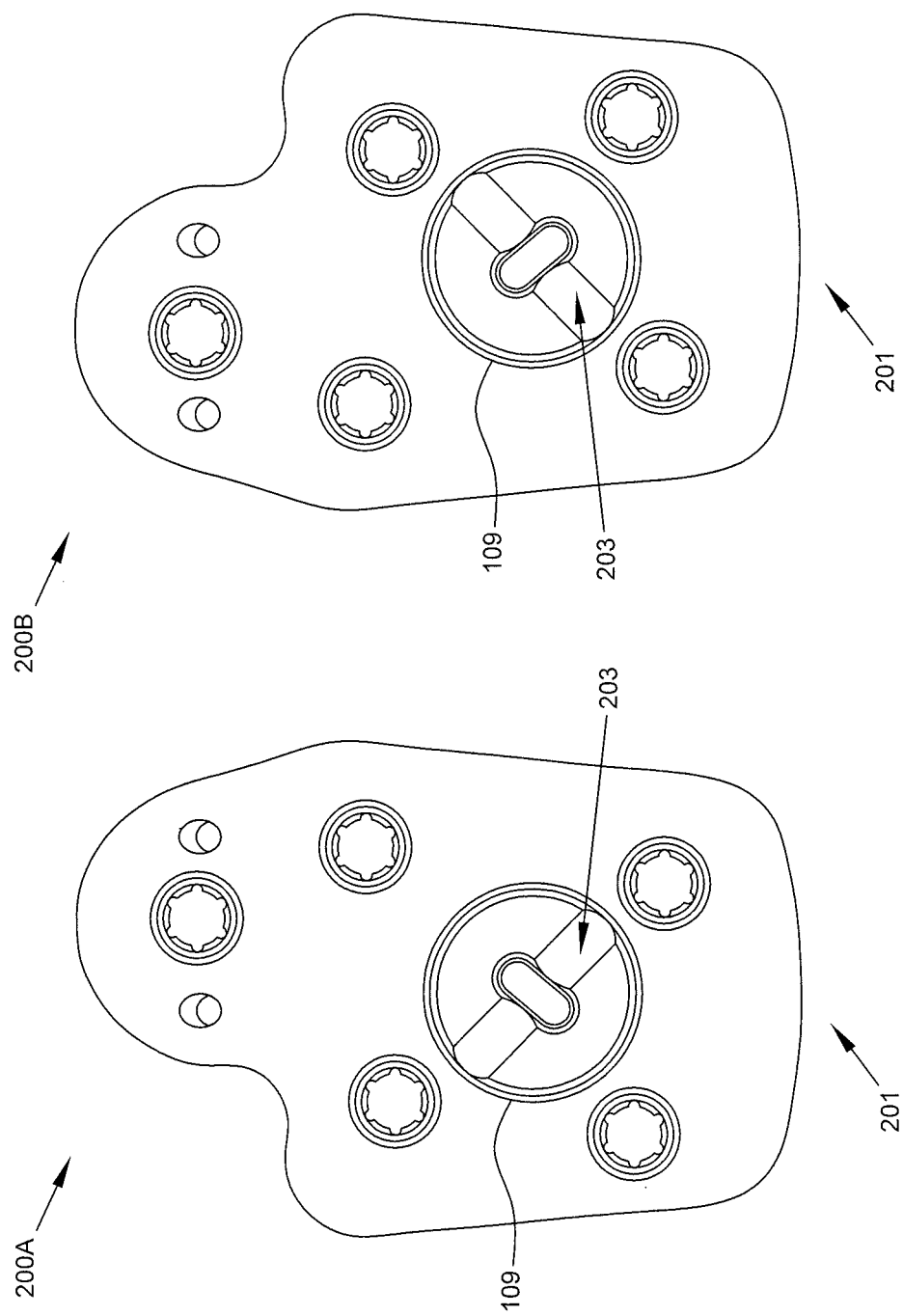

REVISION IMPLANT AUGMENTS, SYSTEMS, AND METHODS

CROSS REFERENCE TO RELATED APPLICATIONS

This application is a continuation of U.S. patent application Ser. No. 15/455,696, filed Mar. 10, 2017, which is a Divisional Application of U.S. patent application Ser. No. 14/403,829 filed Nov. 25, 2014, which is a national phase entry under 35 U.S.C. 371 of international patent application No. PCT/US2014/052301, filed Aug. 22, 2014, the entirety of which is incorporated herein by reference.

FIELD OF DISCLOSURE

The disclosed augments, systems, and methods relate to orthopedic implants. More particularly, the disclosed augments, systems, and methods relate to augment inserts for orthopedic implant revisions.

BACKGROUND

Total joint replacements are orthopedic implants for repairing or replacing a natural joint. Examples of common joints that are replaced by a total joint replacement include, but are not limited to, hips, ankles, and shoulders. The ultimate goal with any total joint sreplacement is to approximate the function and structure of the natural, healthy structures that the implant or prosthesis is replacing.

In many instances, bone adjacent to an implant suffers from bone loss, for example from osteolysis, over a prolonged period of time following a total joint replacement. In some cases, plastic or metal wear particles from operation of the prosthesis trigger an autoimmune reaction which leads to bone resorption. As bone structure is resorbed bone voids are formed which can loosen the fixation of the prosthesis within the patient, causing greater problems for the patient.

SUMMARY

In some embodiments, a revision implant component comprises a body including an inner side and an outer side, tapered such that the width of a front side is greater than the width of a back side, the body defining a plurality of screw holes and having a tapered head configured to engage a talar dome component of a multi-component ankle prosthesis.

In some embodiments, a surgical method includes creating an incision in a patient, exposing a multi-component ankle prosthesis implanted in a patient, disassembling at least one component of the multi-component ankle prosthesis, affixing a revision implant component to non-damaged bone using screws, and coupling the revision implant component to a talar dome of the multi-component ankle prosthesis. The revision implant component has a body including a head configured to engage a feature of a component of the multi-component ankle prosthesis for coupling the revision implant component to the component of the multi-component ankle prosthesis.

In some embodiments, a surgical method includes creating an incision in a patient, exposing a multi-component ankle prosthesis implanted in a patient, disassembling at least one component of the multi-component ankle prosthesis, resecting damaged bone adjacent to the at least one disassembled component of the multi-component ankle prosthesis, selecting a revision implant component from a kit containing a plurality of a revision implant components based on the desired thickness of the selected a revision implant component as a function of the depth of bone resected, affixing the revision implant component to non-damaged bone using screws, and coupling the revision implant component to a talar dome of the multi-component ankle prosthesis. The revision implant component has a body including a tapered head configured to operatively connect with a talar dome of the multi-component ankle prosthesis.

BRIEF DESCRIPTION OF THE DRAWINGS

FIG. 2A is a profile view of the top of one example of a revision implant component in accordance with some embodiments.

FIG. 2B is a profile view of the top of one example of a revision implant component in accordance with some embodiments.

DETAILED DESCRIPTION

Figure 1B:
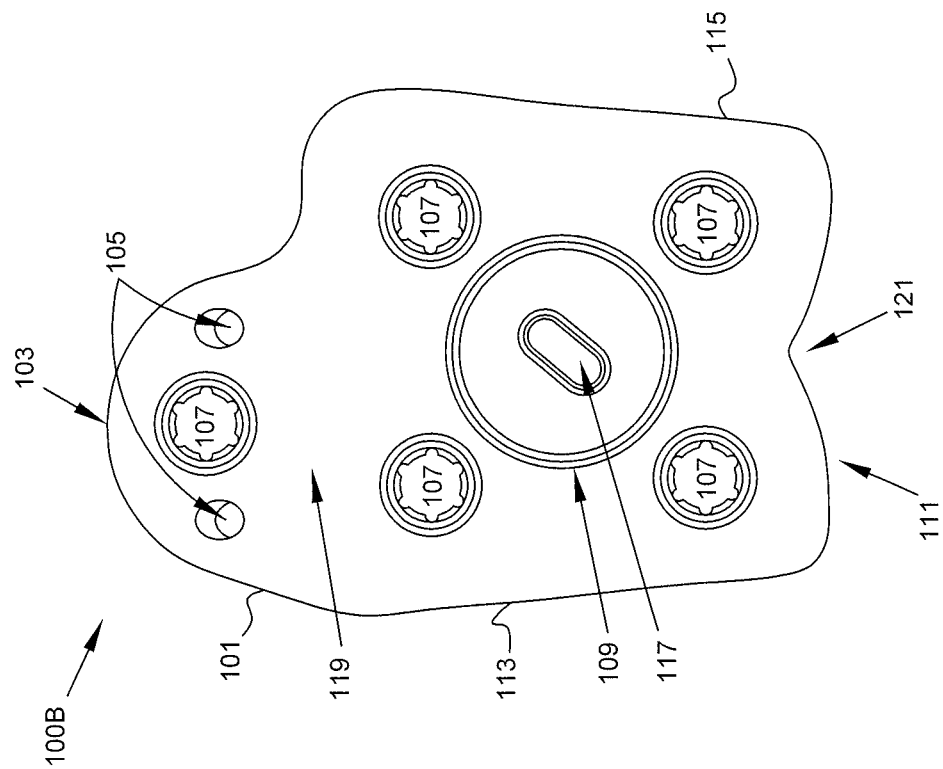
FIG. 1B is a profile view of the top of one example of a revision implant component in accordance with some embodiments.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods advantageously enable revisions of total ankle implants by providing augments designed to be coupled to an original or replacement implant to fill in any gaps formed in the bone. The disclosed systems and methods advantageously provide an effective coupling between the augment and an implant component such as a talar dome, as well as between the augment and bone unaffected by bone loss.

Figure 1A:
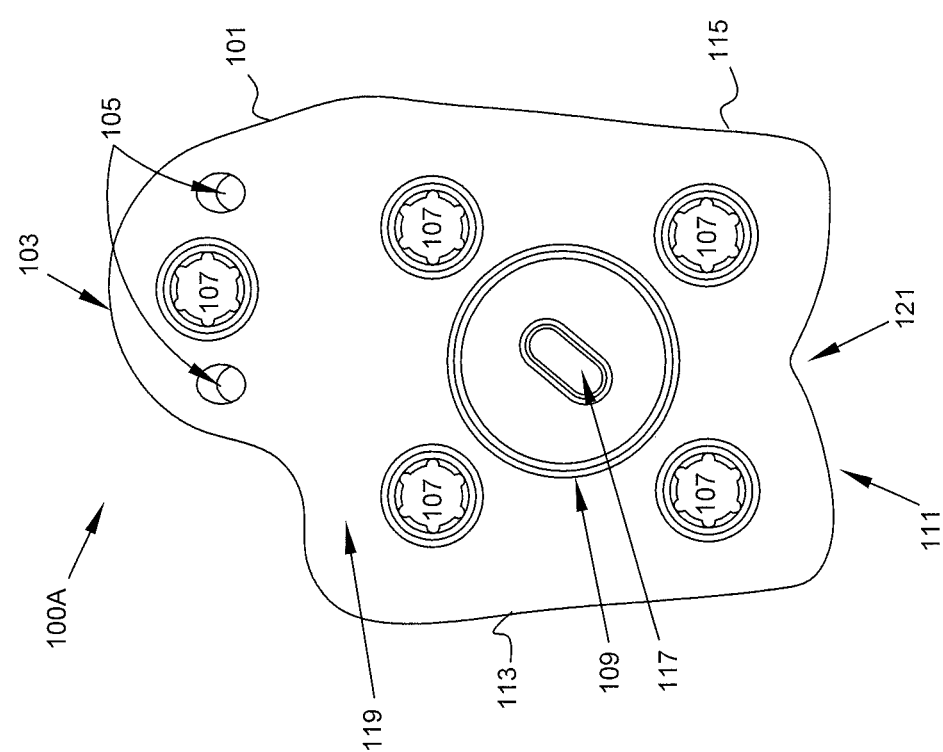
FIG. 1A is a profile view of the top of one example of a revision implant component in accordance with some embodiments.

FIG. 1A illustrates one example of a revision implant component 100A in accordance with some embodiments. FIG. 1A is a profile view of the top of revision implant component 100A. Revision implant component 100A is configured for use with the left ankle joint of a patient.

Revision implant component 100A comprises a body 101 having an inner side 115, outer side 113, front side 103, and back side 111. The body 101 defines a plurality of screw apertures 107 and a pair of wire apertures 105. Body 101 further includes a head 109 which protrudes from upper surface 119.

In some embodiments, the shape of body 101 is configured to match the shape of a talar dome implant. In other embodiments, the shape of body 101 is configured to match the shape of the talus, or to match talar bone unaffected by bone loss. Thus, in some embodiments, such as that illustrated in FIG. 1A, body 101 includes a front side 103 having a bulbous shape and a back side 111 having a sulcus shape or groove 121. In some embodiments, back side 111 has a straight, curved, or bulbous edge shape. Similarly, in some embodiments front side 103 has a straight, curved, or grooved shape so as to match the shape of a talar dome implant or the talus.

Inner side 115 and outer side 113 are tapered from front to back, such that the body 101 is wider near the front side 103 than the back side 111. The taper of inner side 115 and outer side 113 is configured to fill the bone voids and rest on the remaining talar bone.

In some embodiments, screw apertures 107 are threaded. In some embodiments, screw apertures 107 include polyaxial locking tabs. In some embodiments, screw apertures 107 are configured to be used with locking screws having threaded heads.

In some embodiments, body 101 defines at least one wire aperture 105. Wire apertures 105 assist in the proper placement of revision implant component 100A during surgery. Wire apertures 105 can be configured to receive k-wires or similar surgical tools to ensure revision implant component 100A is disposed in the proper location as determined by a surgeon and as guided by surgical instrumentation.

Head 109 is configured as an interference connection to a talar dome. A tapered recess in a talar dome receives the tapered head 109, and an impact connection is made between the talar dome and head 109. In some embodiments, the head 109 is a Morse taper. In some embodiments, head 109 additionally defines a recess 117.

In still further embodiments, head 109 comprises "timed threads" that are configured such that when the threaded head 109 and threaded talar dome are properly connected, a longitudinal passageway is in alignment. Traditional threaded connections accept varying amounts of torque and respond with varying alignments; timed threads ensure a proper connection and a specific alignment so long as applied torque is within a predetermined range.

In some embodiments, the thickness of revision implant component 100A, as measured from upper surface 109 to a substantially parallel back surface (not shown in FIG. 1A, see thickness T in FIG. 4B), is configured to fit the thickness of bone lost. In other embodiments, the thickness of revision implant component 100A is configured to fit the thickness required for proper support of a talar dome implant. In other embodiments, the thickness could be angled or tapered along the length of the implant.

FIG. 1B illustrates a second example of a revision implant component 100B in accordance with some embodiments. Revision implant component 100B is a mirror image of revision implant component 100A, and is therefore configured for use with the right ankle joint of a patient.

FIG. 2A illustrates another example of a revision implant component 200A in accordance with some embodiments. FIG. 2A is a profile view of the top of revision implant component 200A. Revision implant component 200A is configured for use with the left ankle joint of a patient.

Revision implant component 200A is substantially the same as revision implant component 100A described above. However, revision implant component 200A includes a curved back side 201 in place of the groove 121 in back side 111. Additionally, head 109 defines a notch 203. In some embodiments, notch 203 has a diameter that is sized and configured to receive a screw driver or other elongate tool therein. In some embodiments, a screw driver or other elongate tool is used to assist a surgeon in removing the revision implant component 200A.

FIG. 2B illustrates a second example of a revision implant component 200B in accordance with some embodiments. Revision implant component 200B is a mirror image of revision implant component 200A, and is therefore configured for use with the right ankle joint of a patient.

Figure 3B:
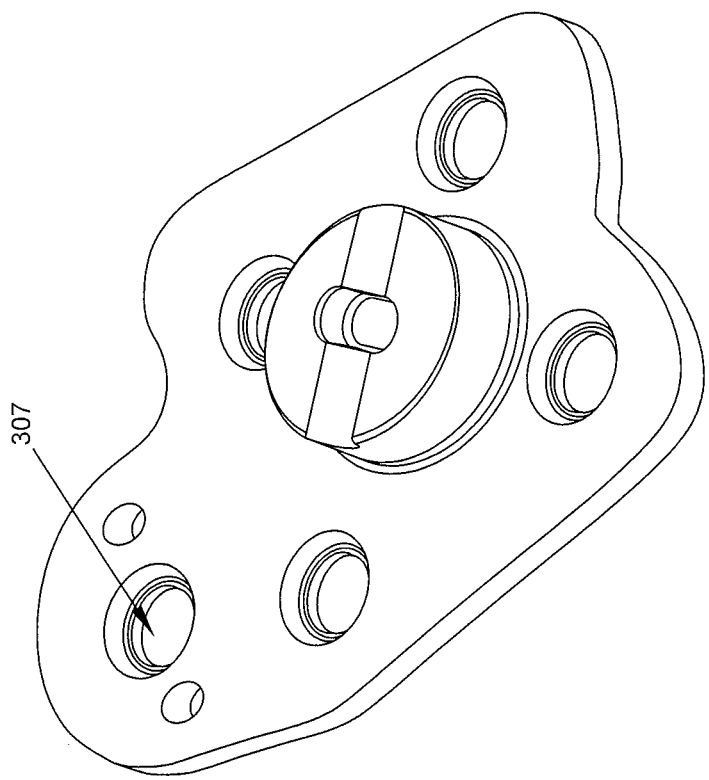
FIG. 3B is an isometric view of one example of a revision implant component in accordance with some embodiments.
Figure 3A:
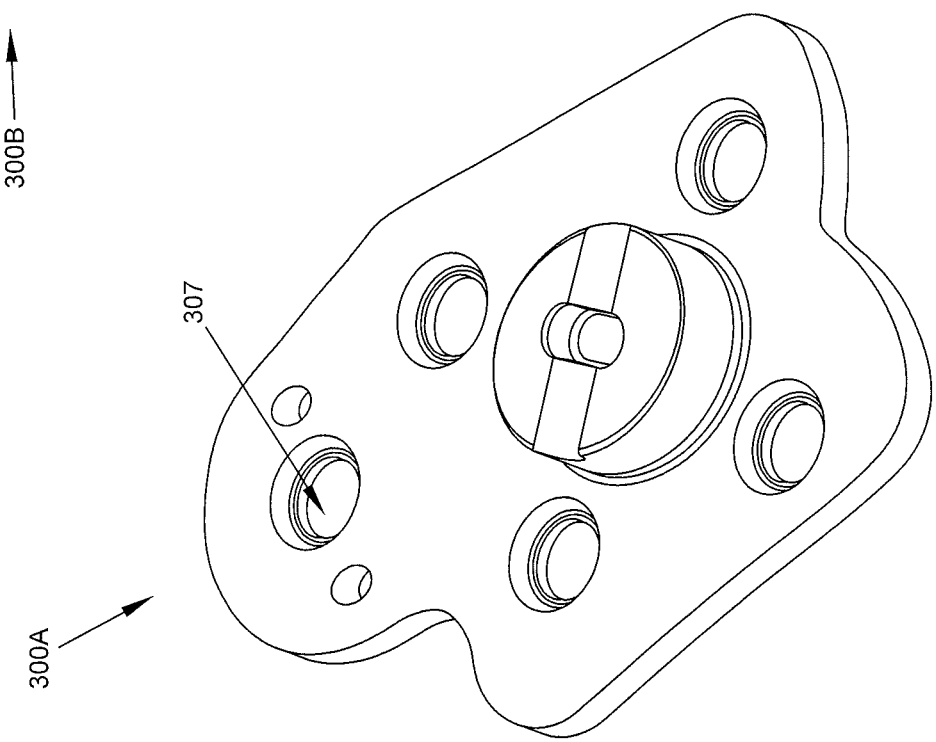
FIG. 3A is an isometric view of one example of a revision implant component in accordance with some embodiments.

FIG. 3A illustrates yet another example of a revision implant component 300A in accordance with some embodiments. FIG. 3A is an isometric view of revision implant component 300A. Revision implant component 300A is configured for use with the left ankle joint of a patient.

Revision implant component 300A is substantially the same as revision implant component 100A described above. However, revision implant component 300A includes an alternate configuration of the plurality of screw apertures 307. In this embodiment, screw apertures 307 lack the polyaxial locking tabs illustrated in FIGS. 1A and 1B. Instead, screw apertures 307 are threaded or include a deformable region adjacent to the aperture designed to contact the threaded head of a locking screw.

FIG. 3B illustrates a second example of a revision implant component 300B in accordance with some embodiments. Revision implant component 300B is a mirror image of revision implant component 300A, and is therefore configured for use with the right ankle joint of a patient.

Figure 4B:
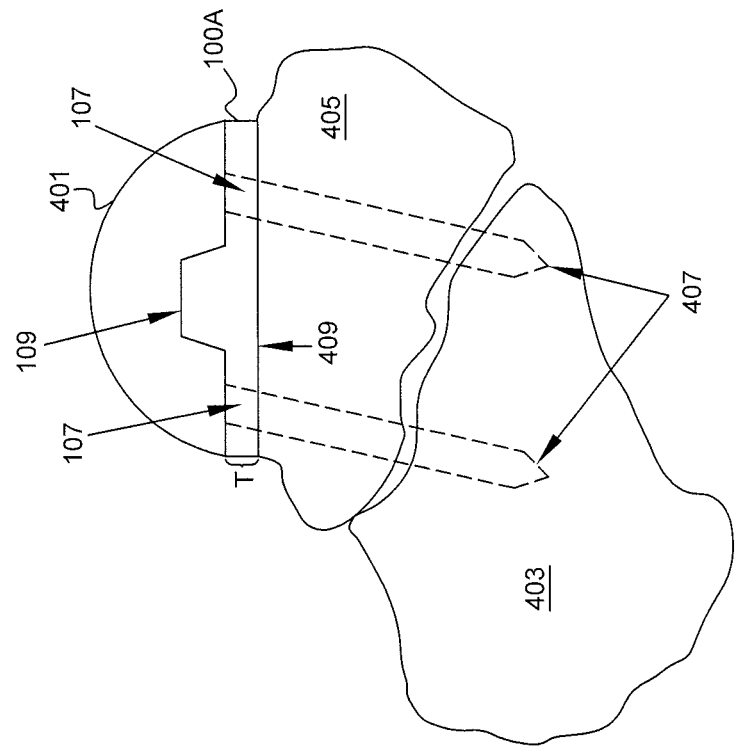
FIG. 4B is a schematic diagram of the placement of a revision implant component in accordance with some embodiments.
Figure 4A:
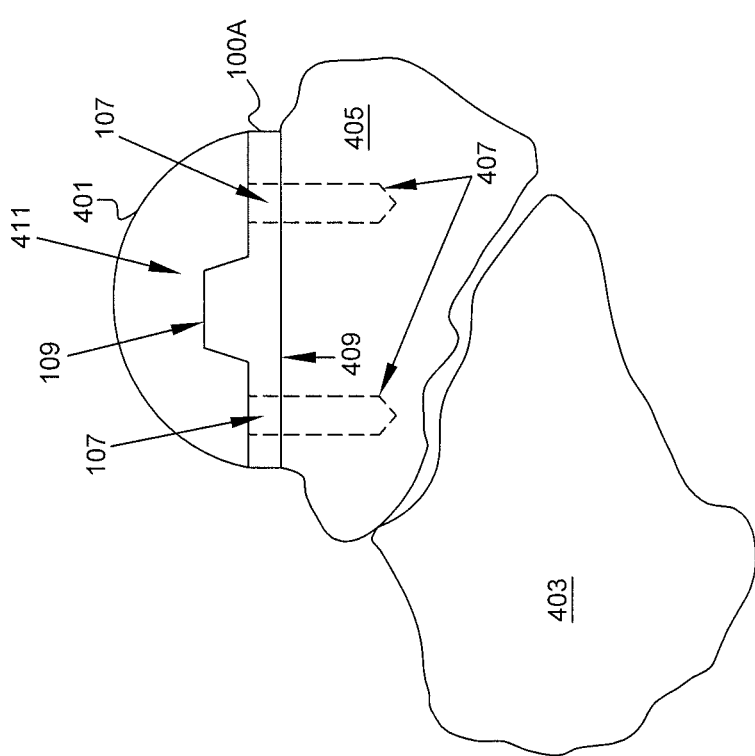
FIG. 4A is a schematic diagram of the placement of a revision implant component in accordance with some embodiments.

FIGS. 4A and 4B are schematic diagrams of the placement of a revision implant component 100A in accordance with some embodiments. During surgery, portions of the talus 405 which were damaged may be resected to form a substantially planar surface 409 of bone which was not damaged (i.e. a surface of healthy or solid bone mass). Revision implant component 100A is affixed to surface 409 using a plurality of screws (not pictured) disposed through screw apertures 107. As illustrated, in some embodiments screw holes 407 are drilled into the talus prior to placement of the revision implant component 100A. In some embodiments, revision implant component 100A is affixed to talus 405 using locking screws with threaded heads. In other embodiments, revision implant component 100A is affixed to talus 405 using non-locking screws, which may provide a compressive force to revision implant component 100A against the talus 405.

Once revision implant component 100A is affixed to talus 405, a talar dome 401 is operably connected to revision implant component 100A. As discussed above, head 109 of revision implant component 100A is tapered to form an interference connection with a recess 411 defined by talar dome 401. In some embodiments, head 109 is a Morse taper. During surgery, the talar dome 401 to revision implant component 100A connection is made in situ. The talar dome 401 is placed on revision implant component 100A with recess 411 aligned with head 409. Talar dome 401 is then impacted to operably connect or bond talar dome 401 with revision implant component 100A.

FIG. 4B is substantially the same as FIG. 4A and shows a placement of a revision implant component 100A. However, in FIG. 4B, screw holes 407 are drilled at a sufficient angle and depth to reach the calcaneus bone 403. In some embodiments, the talus 405 is sufficiently damaged that it is desirable to affix revision implant component 100A through the talus 405 and to the calcaneus 403. In some embodiments, screw holes 407 are drilled at a sufficient angle and depth to reach the navicular bone (not shown)

In some embodiments, a plurality of revision implant components, such as those described above with reference to FIGS. 1A, 1B, 2A, 2B, 3A, and 3B, are provided in a surgical kit. Each of the provided revision implant components may have a varying shape or thickness (as measured from the upper surface to a substantially parallel back surface—see thickness T in FIG. 4B). By providing varying shapes, thicknesses, and angles, the kit allows a surgeon to conduct an intraoperative determination of the best-fitting revision implant component.

Figure 5:
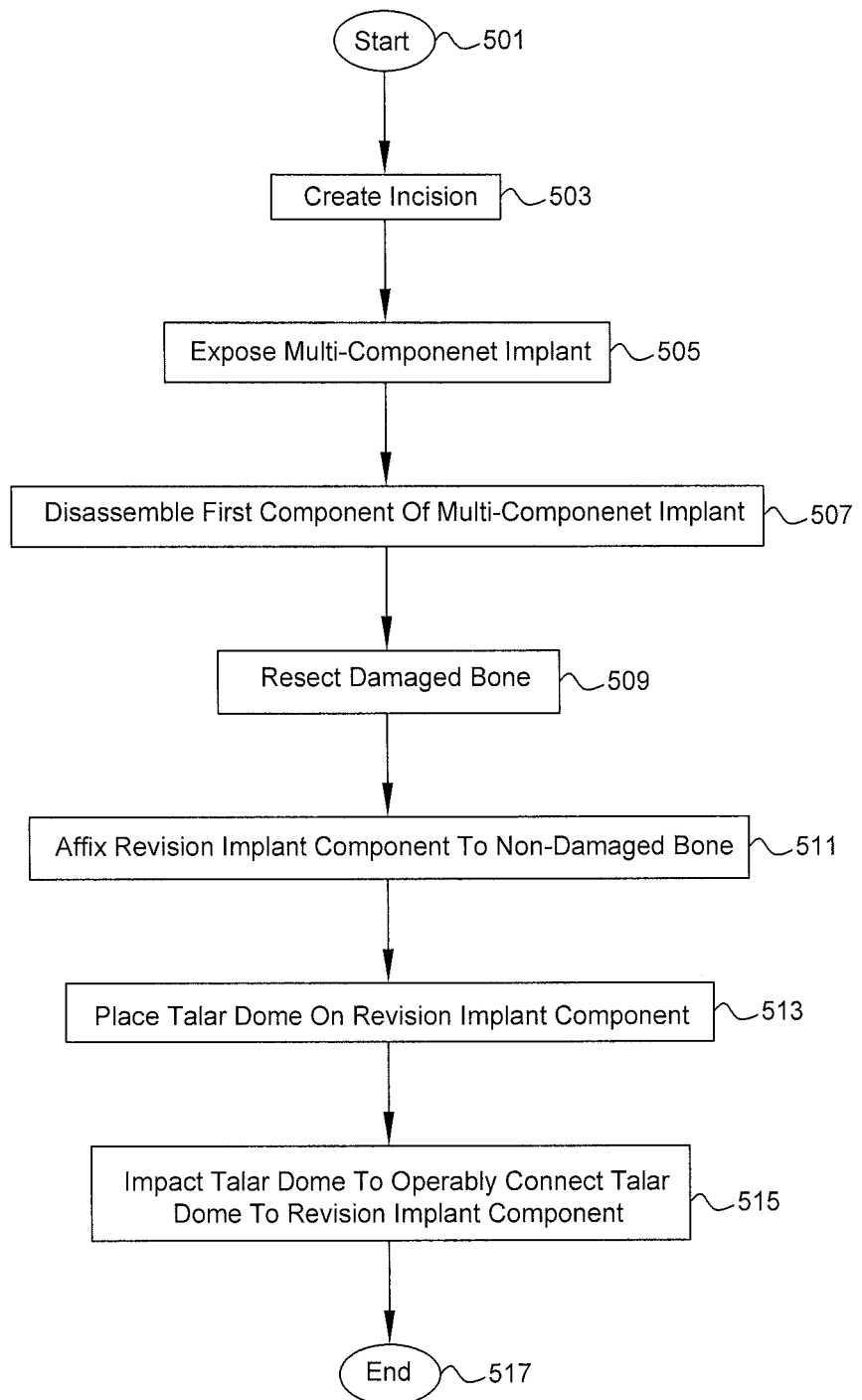
FIG. 5 is a flow diagram of a method in accordance with some embodiments.

A method 500 for implementing a revision implant component is provided in the flow diagram of FIG. 5. The method 500 starts at block 501 and proceeds to block 503, where an incision is made in a patient. At block 505, a multi-component implant which was previously installed in the patient is exposed through the incision.

At block 507, a first component of the multi-component implant is disassembled and removed from the patient, and at block 509 damaged bone is resected in the area adjacent to the prior location of the removed first component. During a revision operation, a multi-component prosthesis that was previously implant in a patient may be partially or completely disassembled. For example, if the multi-component prosthesis is a talar prosthesis, then the talar dome can be decoupled from talar stem by disengaging the Morse taper coupling. When completely disassembled, the entire multi-component prosthesis is removed from the patient.

A revision implant component is affixed to non-damaged bone at block 511. In some embodiments, the revision implant component is affixed to non-damaged bone using locking screws or screws with threaded heads. In other embodiments, the revision implant component is affixed to non-damaged bone using non-locking screws or screws without threaded heads. In other embodiments, the revision implant component is affixed to non-damaged bone using a combination of locking and non-locking screws.

At block 513 a talar dome is placed on the revision implant component and at block 515 the talar dome is operably connected to the revision implant component. In some embodiments, the talar dome is impacted to operably connect the talar dome to the revision implant component. In some embodiments, the connection between talar dome and revision implant component is made in situ following affixation of the revision implant component to non-damaged bone. In other embodiments, the head of a revision implant component and the recess of a talar dome are threaded, and are operably connected in situ. Method 500 ends at block 517.

As described above, the revision implant components/augments can have a variety of shapes and geometries. In some embodiments, the revision implant components/augments are formed from a plasma sprayed titanium, although other materials including, but not limited to, BIOFOAM®, available from Wright Medical Technology, Inc., and other metal, ceramic, plastic, and bone growth materials.

The size and shape of the revision implant component/augment can be selected after pre-operative assessment using fluoroscopy to identify the position of a multi-component prosthesis that is implanted in bone, or the selection of the appropriate revision implant component/augment can be performed intraoperatively by a surgeon or other healthcare provider after reviewing the implant site. In some embodiments, the revision implant components/augments are individually sterilized and packaged while in some embodiments the implant components/augments are provided in a kit. For example, when provided in a kit, each individual implant component/augment may be individually packaged and included in a larger container or packaging. However, kits can also be formed without packing multiple implant components/augments in a single package.

As described above, the revision implant components/augments can have different shapes from each other and/or from the shapes of the components of the multi-component prosthesis such that the revision implant components/augments can be coupled together to fill a void in a bone. Additionally, a single revision implant component/augment can include multiple attachment means such as, for example, a taper, threads, a bayonet coupling, to list but only a few possibilities.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A revision implant component, comprising:
a tapered body shaped and dimensioned to substantially align with a top surface of a resected talus, the body including an inner side and an outer side and defining a plurality of screw holes with a plurality of polyaxial locking tabs disposed about the circumference of the plurality of screw holes, and a head configured to engage a talar dome component of a multi-component ankle prosthesis.

2. The revision implant component of claim 1, wherein the body is shaped and dimensioned to substantially align with a bottom surface of a talar dome.

3. The revision implant component of claim 2, wherein the head is shaped and dimensioned as a Morse taper.

4. The revision implant component of claim 3, wherein the head defines a recess and a notch.

5. The revision implant component of claim 4, wherein the body further defines at least one wire hole.

6. A surgical method, comprising:
creating an incision in a patient;

exposing a multi-component ankle prosthesis implanted in a patient;

disassembling at least one component of the multi-component ankle prosthesis;

affixing a revision implant component to non-damaged bone using screws; and coupling the revision implant component to a talar dome of the multi-component ankle prosthesis, wherein the revision implant component has a tapered body shaped and dimensioned to substantially align with a top surface of a resected talus, the body including an inner side and an outer side and defining a plurality of screw holes with a plurality of polyaxial locking tabs disposed about the circumference of the plurality of screw holes, and a head configured to engage a talar dome component of a multi-component ankle prosthesis.

7. The surgical method of claim 6, further comprising resecting damaged bone prior to the step of affixing a revision implant component to non-damaged bone using screws.

8. The surgical method of claim 7, wherein the revision implant component is affixed to non-damaged bone using screws with threaded heads.

9. The surgical method of claim 8, wherein the screws are affixed to the revision implant component and non-damaged bone of the talus.

10. The surgical method of claim 9, wherein the screws are affixed to the revision implant component and non-damaged bone of the calcaneus or navicular.

11. The surgical method of claim 10, wherein the step of coupling the revision implant component to a talar dome further comprises attaching an augment between the revision implant component and the talar dome.

12. The surgical method of claim 7, wherein the step of affixing the revision implant component to non-damaged bone further comprises attaching an augment between the revision implant component and the non-damaged bone.

13. The surgical method of claim 7, wherein the revision implant component is coupled to the component of the multi-component ankle prosthesis in situ.

* * * * *